(12) United States Patent
Merianos et al.

(10) Patent No.: US 7,740,876 B2
(45) Date of Patent: Jun. 22, 2010

(54) ANTIMICROBIAL COMPOSITION OF 3-IODO-2-PROPYNYLBUTYL CARBAMATE AND 1,3-BUTYLENE GLYCOL AS SOLVENT

(75) Inventors: John J. Merianos, Wayne, NJ (US); Paul Garelick, South Plainfield, NJ (US); Susan M. Lindstrom, Ramsey, NJ (US)

(73) Assignee: ISP Investments Inc., Wilmington, DE (US)

( * ) Notice: Subject to any disclaimer, the term of this patent is extended or adjusted under 35 U.S.C. 154(b) by 640 days.

(21) Appl. No.: 11/439,702

(22) Filed: May 23, 2006

(65) Prior Publication Data

US 2007/0274944 A1 Nov. 29, 2007

(51) Int. Cl.
*A01N 25/00* (2006.01)
*A01N 25/34* (2006.01)
*A01N 31/00* (2006.01)
*A01N 47/10* (2006.01)
*A01N 29/02* (2006.01)

(52) U.S. Cl. ............ 424/405; 424/404; 514/470; 514/476; 514/745; 514/724; 435/243; 435/252.1

(58) Field of Classification Search ............ 514/476, 514/479, 478, 745, 724; 435/243, 252.1; 424/405, 404
See application file for complete search history.

(56) References Cited

U.S. PATENT DOCUMENTS

| | | | | |
|---|---|---|---|---|
| 5,552,425 A | * | 9/1996 | Merianos | 514/390 |
| 5,631,273 A | * | 5/1997 | Merianos | 514/389 |
| 2003/0039580 A1 | * | 2/2003 | Borokhov et al. | 422/37 |

* cited by examiner

*Primary Examiner*—Sandra Saucier
*Assistant Examiner*—Susan Hanley
(74) *Attorney, Agent, or Firm*—William I. Davis; Thompson Hine LLP

(57) ABSTRACT

An antimicrobial composition of 3-iodo-2-propynylbutyl carbamate (IPBC) and 1,3-butylene glycol (BG) as solvent, in a defined weight ratio, preferably 9-11% IPBC and 89-91% BG, and personal care formulations including the composition in an amount of about 0.1-0.2% therein, at a pH of 4-9, is described.

15 Claims, No Drawings

ANTIMICROBIAL COMPOSITION OF 3-IODO-2-PROPYNYLBUTYL CARBAMATE AND 1,3-BUTYLENE GLYCOL AS SOLVENT

BACKGROUND OF THE INVENTION

1. Field of the Invention

This invention relates to preservative compositions for inhibiting the growth of microorganisms and fungi in personal care and industrial applications, and, more particularly, to preservative compositions which are effective and safe, are formaldehyde-free and paraben-free, are temperature and pH stable, and have broad compatibility with raw materials present therein.

2. Description of the Prior Art

Preservative compositions having antibacterial properties suitable for use in personal care and industrial applications have been described in the literature, see U.S. Pat. Nos. 3,923,870; 4,844,891; 5,428,050; 5,496,842; 5,552,425; 5,631,273; 6,582,627; and Published Application No. 2003/0039580.

However, each personal care formulation requires a preservative system that meets its specific needs, particularly for effective and safe preservation as determined by challenge testing.

SUMMARY OF THE INVENTION

What is described herein is an antimicrobial composition consisting essentially of 3-iodo-2-propynylbutyl carbamate (IPBC) in 1,3-butylene glycol (BG) as solvent, preferably, by wt., 9-11% IPBC in 89-91% BG, and personal care formulations containing 0.1-0.2% by wt. of the preservative composition, at a pH of 4-9 of the composition.

The preservative compositions herein are effective and safe, are formaldehyde-free and paraben-free, are temperature and pH stable, and are compatible with raw materials present in both personal care and industrial products.

DETAILED DESCRIPTION OF THE INVENTION

The invention will now be illustrated in more detail by the following examples.

EXAMPLE 1

| | NON-IONIC MOISTURIZER | | |
|---|---|---|---|
| PHASE | INGREDIENT | % W/W | SUPPLIER |
| A | Deionized Water | 78.70 | |
| | Disodium EDTA (Versene NA) | 0.10 | Dow |
| | Glycerin (and) Glyceryl Acrylate/Acrylic Acid Copolymer (and) Butylene Glycol (and) PVM/MA Copolymer (LUBRAJEL ® OIL BG) | 0.50 | ISP |
| | Sodium Polyacrylate (RAPITHIX ® A-100) | 0.75 | ISP |
| B | Octyldodecyl Stearate (CERAPHYL ® ODS) | 3.50 | ISP |
| | Isostearyl Neopentanoate (CERAPHYL ® 375) | 3.50 | ISP |
| | Diisopropyl Adipate (CERAPHYL ® 230) | 2.50 | ISP |
| | Ethylhexyl Palmitate (CERAPHYL ® 368) | 2.50 | ISP |
| | $C_{12-15}$ Alkyl Lactate (CERAPHYL ® 41) | 3.00 | ISP |
| | Glyceryl Stearate (and) Laureth-23 (CERASYNT ® 945) | 1.25 | ISP |
| | Peg-20 Stearate (CERASYNT ® 840) | 1.00 | ISP |
| C | Cyclopentasiloxane (SI-TEC ™ CM 040) | 2.50 | ISP |
| D | 1,3-Butylene Glycol and Iodopropynyl Butylcarbamate (LIQUAGARD ™) | 0.20 | ISP |
| | | 100.00% | |

Procedure

1. Combine Phase A except for Rapithix A-100. Sprinkle in Rapithix A-100 with good mixing.
2. Combine Phase B with mixing and heat to 70° C.
3. When Phase A is uniform and Phase B is at 70° C. slowly add Phase B to Phase A with good mixing.
4. When batch is uniform add Phase C with good mixing.
5. Add Phase D and mix until the batch is completely uniform.

Challenge Tests

The challenge test is a 28-day test used to verify the effectiveness of a preservative system in a personal care formulation. Selected personal care formulations were inoculated with microorganisms at the onset of testing (0 hours), then sampled at 48 hours, 7 days, 14 days, 21 days, and 28 days. At 21 days the formulations were re-inoculated with the same microorganisms. Pass/fail criteria were based on modified Cosmetic, Toiletry and Fragrance Association (CTFA) protocol.

The invention composition was tested in several systems and found to effectively preserve a variety of personal care formulations against the following microorganisms:

| Microorganism | Abbreviation |
|---|---|
| *Candida albicans* | CAN |
| *Aspergillus niger* | AN |

| Inoculum Concentration (CFU/g) | | |
|---|---|---|
| Organism | 0 Hours | 21 Days |
| CAN ATCC 10231 | $1.9 \times 10^6$ | $5.0 \times 10^5$ |
| AN ATCC 16404 | $3.0 \times 10^5$ | $1.0 \times 10^6$ |

| Preservative Efficacy Test Results (CFU/g) | | | | | |
|---|---|---|---|---|---|
| Organism | 48 Hrs | 7 Days | 14 Days | 21 Days | 28 Days |
| CAN ATCC 10231 | $>1.0 \times 10^6$ | <10 | <10 | $1.0 \times 10^2$ | <10 |

-continued

| Preservative Efficacy Test Results (CFU/g) | | | | | |
|---|---|---|---|---|---|
| Organism | 48 Hrs | 7 Days | 14 Days | 21 Days | 28 Days |
| AN ATCC 16404 | <10 | <10 | <10 | <10 | <10 |

Accordingly this formulation of Example 1 passed a 28-day double challenge efficacy test.

Based on this challenge test data, Liquagard™ is recommended for use in personal care products at levels between 0.1%-0.2% within a broad pH range of 4.0-9.0.

EXAMPLE 2

SHOWER GEL

| PHASE | INGREDIENT | % W/W | SUPPLIER |
|---|---|---|---|
| A | Deionized Water | 51.45 | |
| | Disodium EDTA | 0.10 | Dow Chemical |
| | Polyquaternium-7 (CONDITIONEZE ® 7) | 2.50 | ISP |
| | Glycerin | 2.50 | |
| | Benzophenone-4 (ESCALOL ® 577) | 0.20 | ISP |
| B | Ammonium Lauryl Sulfate | 30.00 | Rhodia |
| | Cocamidopropyl Betaine | 10.00 | Goldschmidt |
| | Cocamide DEA | 2.50 | Cognis |
| C | PEG-7 Glyceryl Cocoate | 0.30 | Cognis |
| | Fragrance (#01779396) | 0.10 | Dragoco |
| | Blue #1 (.1% Aq. Solution) | 0.20 | Warner Jenkinson |
| D | 1,3-Butylene Glycol and Iodopropynyl Butylcarbamate (Liquagard ™) | 0.15 | ISP |
| | | 100.00% | |

Procedure
1. Combine Phase A with mixing and begin heating to 65° C.
2. When Phase A is uniform add Phase B in the order listed with mixing.
3. Start cooling the batch.
4. Add Phases C & D at 30° C. with mixing.
5. QS for water loss and mix to RT.

pH=7.6 Viscosity=7,200 cps (Brookfield Model RVT, TB @ 5 RPM)

| Inoculum Concentration (CFU/g) | | |
|---|---|---|
| Organism | 0 Hours | 21 Days |
| CAN ATCC 10231 | 4.9 × 10$^6$ | 6.6 × 10$^6$ |
| AN ATCC 16404 | 1.0 × 10$^6$ | 2.4 × 10$^6$ |

| Preservative Efficacy Test Results (CFU/g) | | | | | |
|---|---|---|---|---|---|
| Organism | 48 Hrs | 7 Days | 14 Days | 21 Days | 28 Days |
| CAN ATCC 10231 | <10 | <10 | <10 | <10 | <10 |
| AN ATCC 16404 | <10 | <10 | <10 | <10 | <10 |

The formulation of Example 2 passed the 28-day double challenge efficacy test.

EXAMPLE 3

PRODUCT: Shower Gel
USE LEVEL: 0.02% Liquagard (200 ppm active IPBC)

| TEST ORGANISM | INOCULUM (0 hours) | REINOCULUM (21 days) |
|---|---|---|
| Candida albicans 10231 | 4.9 × 10$^6$ cfu/g of product | 6.6 × 10$^6$ cfu/g |
| Aspergillus niger 16404 | 1.0 × 10$^6$ cfu/g of product | 2.4 × 10$^6$ cfu/g |

| | Assay Interval | | | | |
|---|---|---|---|---|---|
| Test Organism | 48 Hrs | 7 Days | 14 Days | 21 Days | 28 Days |
| Candida albicans | <10 | <10 | <10 | <10 | <10 |
| Aspergillus niger | <10 | <10 | <10 | <10 | <10 |

EXAMPLE 4

SCREENING EMULSION

| PHASE | INGREDIENT | W/W % |
|---|---|---|
| A | Stearic acid | 5.00 |
| | Mineral oil | 2.50 |
| | Cetyl alcohol, NF | 1.00 |
| | Ceteareth-5 | 0.50 |
| | Glyceryl Stearate and PEG-100 Stearate | 1.50 |
| B | DI water | 87.90 |
| | Triethanolamine (99%) | 1.00 |
| C | 1,3-Butylene Glycol (and) Iodopropynyl Butylcarbamate (LIQUAGARD ™) | 0.10 |
| D | Citric acid 30% aqueous | 0.60 |

Procedure:
1. Heat Phase A to 75° C. Heat Phase B to 75° C.
2. Add Phase A to B under moderate sheer with overhead mixer. Remove heat and continue mixing throughout preparation.
3. Add Phase C at the appropriate temperature (° C.).
4. Add Phase D at 35-40° C.
5. Cool to 30-35° C.

6. QS with water. Remove contents to a storage container reserving enough in the beaker to measure a pH. Store in refrigerator.

EXAMPLE 5

Antifungal Efficacy Data

Formulation: Screening Emulsion
Liquagard: 10% IPBC in 1,3 butylene glycol
Test Method: MLM 100-9

Inoculate formulation at 0 hours. Assay at 48 hours, 7 days, 14 days, 21 days. Re-inoculate at 21 days and then final assay at 28 days. Inoculum counts are listed in Table I. Two levels of Liquagard were tested; the data is contained in Tables II and III below.

TABLE I

| TEST ORGANISM | INOCULUM (0 hours) | REINOCULUM (21 days) |
|---|---|---|
| *Aspergillus niger* 16404 | $2.0 \times 10^5$ cfu/g | $3.8 \times 10^5$ cfu/g |
| *Taloromyces luteus* | $3.9 \times 10^4$ cfu/g | $4.0 \times 10^6$ cfu/g |
| *Candida albicans* 10231 | $2.0 \times 10^6$ cfu/g | $1.5 \times 10^6$ cfu/g |

TABLE II

| | 0.05% Liquagard (50 ppm IPBC) | | | | |
|---|---|---|---|---|---|
| Test Organism | 48 Hrs | 7 Days | 14 Days | 21 Days | 28 Days |
| *A. niger* | <10 | <10 | <10 | <10 | <10 |
| *T. luteus* | <10 | <10 | <10 | <10 | <10 |
| *C. albicans* | <10 | <10 | <10 | <10 | <10 |

TABLE III

| | 0.1% Liquagard (100 ppm IPBC) | | | | |
|---|---|---|---|---|---|
| Test Organism | 48 Hrs | 7 Days | 14 Days | 21 Days | 28 Days |
| *A. niger* | <10 | <10 | <10 | <10 | <10 |
| *T. luteus* | <10 | <10 | <10 | <10 | <10 |
| *C. albicans* | <10 | <10 | <10 | <10 | <10 |

EXAMPLE 6

Liquagard vs Controls

PRODUCT: Screening emulsion
USE LEVEL: 100 ppm active IPBC

| TEST ORGANISM | INOCULUM (0 hours) | REINOCULUM (21 days) |
|---|---|---|
| *Candida albicans* 10231 | $7.2 \times 10^6$ cfu/g of product | $3.0 \times 10^6$ cfu/g |
| *Aspergillus niger* 16404 | $1.5 \times 10^6$ cfu/g of product | $7.0 \times 10^6$ cfu/g |

| | Assay Interval | | | | |
|---|---|---|---|---|---|
| Test Organism | 48 Hrs | 7 Days | 14 Days | 21 Days | 28 Days |
| Liquagard ™ | | | | | |
| *Candida albicans* | <10 | <10 | <10 | <10 | <10 |
| *Aspergillus niger* | <10 | <10 | <10 | <10 | <10 |
| Glycacil L* (Lonza) | | | | | |
| *Candida albicans* | <10 | <10 | <10 | <10 | <10 |
| *Aspergillus niger* | <10 | <10 | <10 | <10 | <10 |
| Unpreserved | | | | | |
| *Candida albicans* | >1E6 | >1E6 | >1E6 | | |
| *Aspergillus niger* | >1E6 | >1E6 | >1E6 | | |

*Glycacil L - polyethylene glycol monococoate (~40%), polyethylene glycol dicocoate (~40%), 3-iodo-2-propynyl butyl carbamate (~10%) and polyethylene glycol (~10%).

EXAMPLE 7

| | NON-IONIC EMULSION | | |
|---|---|---|---|
| PHASE | INGREDIENT | % W/W | SUPPLIER |
| A | Deionized Water | 70.10 | |
| | PVM/MA Decadiene Crosspolymer (Stabileze ® QM) | 0.20 | ISP |
| B | Ethylhexyl Palmitate (Ceraphyl ® 368) | 10.00 | ISP |
| | Cetearyl Alcohol and Ceteareth-20 (Promulgen D) | 2.00 | Amerchol |
| | Glyceryl Stearate and Laureth 23 (Cerasynt ® 945) | 2.50 | ISP |
| | Isocetyl Stearate (Ceraphyl ® 494) | 10.00 | ISP |
| C | Triethanolamine (99%) | 0.20 | |
| | Deionized Water | qs | |
| | 1,3-Butylene Glycol and Iodopropynyl Butylcarbamate (Liquagard ™) | 0.20 | ISP |
| | | 100.00% | |

Procedure:
1. Sprinkle Stabileze into water with stirring at RT. Heat phase A to 75° C.
2. Combine Phase B, heat to 85° C.
3. Combine Phase B to A with stirring, at 75° C.
4. When batch is uniform add Phase C.
5. When uniform turn off heat.
6. Continue stirring thru cool down.
7. Make up water loss and stir at RT. Store in refrigerator.

EXAMPLE 8

Liquagard vs Controls

PRODUCT: Nonionic Emulsion
USE LEVEL: 200 ppm active IPBC

| TEST ORGANISM | INOCULUM (0 hours) | REINOCULUM (21 days) |
|---|---|---|
| *Candida albicans* 10231 | $7.2 \times 10^6$ cfu/g of product | $3.0 \times 10^6$ cfu/g |
| *Aspergillus niger* 16404 | $1.5 \times 10^6$ cfu/g of product | $7.0 \times 10^5$ cfu/g |

| Test Organism | Assay Interval | | | | |
|---|---|---|---|---|---|
| | 48 Hrs | 7 Days | 14 Days | 21 Days | 28 Days |
| Liquagard ™ | | | | | |
| Candida albicans | $3.1 \times 10^4$ | <10 | <10 | <10 | <10 |
| Aspergillus niger | $5.0 \times 10^4$ | <10 | <10 | <10 | <10 |
| Control - Glycacil L | | | | | |
| Candida albicans | $8.5 \times 10^5$ | <10 | <10 | <10 | $3.0 \times 10^1$ |
| Aspergillus niger | $1.9 \times 10^5$ | <10 | <10 | <10 | <10 |
| Unpreserved | | | | | |
| Candida albicans | >1.E6 | >1E6 | >1E6 | | |
| Aspergillus niger | >1E6 | >1E6 | >1E6 | | |

In summary, the invention Liquagard™ (ISP) composition can be effectively used in personal care compositions including:

Skin Care Compositions

Sunscreen creams and lotions; moisturizers; night creams; hand/body creams and lotions; shaving products; cleansing products; wipes; foundations; concealers; body washes; shower gels; liquid hand soaps and baby products.

Hair Care Compositions

Shampoos, conditioners; deep conditioning treatments; styling gels, mousses, shine lotions, hair colorants and baby products.

While the invention has been described with particular reference to certain embodiments thereof, it will be understood that changes and modifications may be made which are within the skill of the art. Accordingly, it is intended to be bound only by the following claims, in which:

What is claimed is:

1. An antimicrobial composition consisting of, by wt., 9-11% 3-iodo-2-propynylbutyl carbamate (IPBC) and 89-91% 1,3-butylene glycol.
2. A formulation comprising a personal care formulation including the antimicrobial composition of claim 1.
3. A formulation comprising a personal care formulation containing 0.1-0.2% by wt. of the antimicrobial composition of claim 1.
4. A formulation according to claim 3 at a pH of 4-9.
5. A formulation according to claim 2 which is a skin care product.
6. A formulation according to claim 2 which is a hair care product.
7. A formulation according to claim 5 which is a non-ionic moisturizer.
8. A formulation according to claim 2 which is a shower gel.
9. A formulation according to claim 2 which is a non-ionic emulsion.
10. A product comprising an industrial product which includes the antimicrobial composition of claim 1.
11. An antimicrobial composition comprising 3-iodo-2-propynylbutyl carbamate (IPBC) in 1,3-butylene glycol as a solvent wherein said antimicrobial composition comprises, by wt., 9-11% IPBC and 89-91% 1,3-butylene glycol.
12. A formulation comprising a personal care formulation comprising the antimicrobial composition of claim 11.
13. A formulation in accordance with claim 12 wherein said personal care formulation is selected from the group consisting of skin care products and hair care products.
14. A formulation comprising a personal care formulation comprising 0.1-0.2% by weight of the antimicrobial composition of claim 11.
15. A formulation comprising a personal care formulation comprising 0.1-0.2% by weight of the antimicrobial composition of claim 1.

* * * * *